US012796898B2

(12) United States Patent
Pryl et al.

(10) Patent No.: US 12,796,898 B2
(45) Date of Patent: Nov. 17, 2026

(54) CONTROL MECHANISMS FOR ARTICULATABLE MEDICAL DEVICES

(71) Applicant: Verathon Inc., Bothell, WA (US)

(72) Inventors: Matthew Pryl, North Vancouver (CA); Frazer Closson, Burnaby (CA); Alex Antonio, Burnaby (CA)

(73) Assignee: Verathon Inc., Bothell, WA (US)

( * ) Notice: Subject to any disclaimer, the term of this patent is extended or adjusted under 35 U.S.C. 154(b) by 129 days.

(21) Appl. No.: 18/901,482

(22) Filed: Sep. 30, 2024

(65) Prior Publication Data

US 2025/0120577 A1 Apr. 17, 2025

Related U.S. Application Data

(60) Provisional application No. 63/590,621, filed on Oct. 16, 2023.

(51) Int. Cl.
*A61B 1/005* (2006.01)
*A61M 25/01* (2006.01)

(52) U.S. Cl.
CPC .......... *A61B 1/0052* (2013.01); *A61B 1/0057* (2013.01); *A61M 25/0136* (2013.01); *A61M 25/0147* (2013.01)

(58) Field of Classification Search
CPC .................................................... A61B 1/0052
See application file for complete search history.

(56) References Cited

U.S. PATENT DOCUMENTS 3,610,231 A 10/1971 Takahashi et al.
5,888,192 A * 3/1999 Heimberger ....... G02B 23/2476 600/146

(Continued)

FOREIGN PATENT DOCUMENTS

CA 3043908 C 3/2024
EP 3202303 A1 8/2017

(Continued)

OTHER PUBLICATIONS

Office Action issued for Canadian Patent Application No. 3,255,916 dated Dec. 29, 2025, 8 pages.

(Continued)

*Primary Examiner* — Michael J Carey
*Assistant Examiner* — Stephen Floyd London
(74) *Attorney, Agent, or Firm* — Duane Morris LLP

(57) ABSTRACT

An endoscope device comprises a handle, a shaft projecting from the handle, a flexible tip coupled to the distal portion of the shaft; and first and second pull wires extending from the handle portion through the shaft portion and coupled to the flexible tip. The handle portion includes a control wheel assembly coupled to proximal ends of the first and second pull wires. The control wheel assembly comprises a control wheel having a disc-shaped body rotationally mounted within the handle and having an outer perimeter and a first surface and first and second pull wire troughs provided on the first surface for receiving the proximal ends of the first and second pull wires, respectively. Positioning of the first and second pull wires within the first and second pull wire troughs is performed independently to provide accurate tensioning of the first and second pull wires during assembly of the endoscope device.

15 Claims, 12 Drawing Sheets

(56) References Cited

U.S. PATENT DOCUMENTS

| | | | | |
|---|---|---|---|---|
| 7,615,956 | B2 | 11/2009 | Tsusaka | |
| 8,137,308 | B2 | 3/2012 | Schultz | |
| 10,493,238 | B2 | 12/2019 | Selkee | |
| 10,737,064 | B1 | 8/2020 | Ju | |
| 11,324,395 | B2 | 5/2022 | Banik et al. | |
| 11,357,391 | B2 | 6/2022 | Nakao et al. | |
| 2010/0249497 | A1 | 9/2010 | Peine et al. | |
| 2013/0137928 | A1 | 5/2013 | Karasawa et al. | |
| 2014/0200560 | A1 | 7/2014 | Lavender | |
| 2014/0265313 | A1 | 9/2014 | Durr et al. | |
| 2017/0035993 | A1* | 2/2017 | Quinn | A61B 17/00234 |
| 2017/0238787 | A1* | 8/2017 | Hijihara | A61B 1/0052 |
| 2017/0245933 | A1* | 8/2017 | Graham | A61B 17/29 |
| 2019/0142413 | A1 | 5/2019 | Fairneny | |
| 2021/0007582 | A1* | 1/2021 | Graveley | A61B 1/0052 |
| 2021/0212553 | A1 | 7/2021 | Appling et al. | |
| 2021/0212556 | A1 | 7/2021 | Nguyen et al. | |
| 2021/0235973 | A1 | 8/2021 | Gray et al. | |
| 2023/0037743 | A1* | 2/2023 | Hallauer | A61B 1/0011 |
| 2023/0042893 | A1* | 2/2023 | Golden | A61B 1/0052 |
| 2023/0108741 | A1* | 4/2023 | Kawakami | A61B 1/0057 600/146 |
| 2023/0128083 | A1* | 4/2023 | Cornia | A61B 1/008 600/131 |
| 2024/0122457 | A1* | 4/2024 | Lee | A61B 1/0057 |
| 2024/0324861 | A1* | 10/2024 | Jensen | A61B 1/0052 |
| 2024/0366075 | A1 | 11/2024 | Yi et al. | |
| 2025/0151985 | A1* | 5/2025 | Jin | A61B 1/00131 |

FOREIGN PATENT DOCUMENTS

| | | | |
|---|---|---|---|
| JP | 2012249862 | A | 12/2012 |
| JP | 2014168668 | A | 9/2014 |
| WO | 2016189964 | A1 | 12/2016 |
| WO | WO2022133244 | A1 | 6/2022 |
| WO | 2023103930 | A1 | 6/2023 |

OTHER PUBLICATIONS

Awake Bronchoscopic Intubation: Module 1—The Bronchoscope—Toronto General Hospital Department of Anesthesia, Perioperative Interactive Education (PIE) Toronto; accessed online Sep. 27, 2024, 7 pages.

Office Action issued for Japanese Patent Application No. 2024-178559 dated Jan. 8, 2026, 8 pages.

* cited by examiner

CONTROL MECHANISMS FOR ARTICULATABLE MEDICAL DEVICES

BACKGROUND

An endoscope refers to a medical device that allows remote examination of the interior of a patient's body. Endoscopes may be used for a variety of diagnostic and treatment procedures relating, for example, to the gastrointestinal, respiratory, reproductive, and urinary tract systems. To increase the ability to view particular internal structures, endoscopes having articulated tips have been designed. However, such articulated endoscopes suffer from problems relating to precision of the movement of the articulated tip.

DETAILED DESCRIPTION OF THE PREFERRED EMBODIMENTS

The following detailed description refers to the accompanying drawings. The same reference numbers in different drawings may identify the same or similar elements. Also, the following detailed description does not limit the invention.

A video-based endoscope or catheter systems are described that allow for examination of a patient's airway to facilitate placement of endotracheal devices (e.g., an endotracheal tube, etc.), delivery of medicine, etc. The system employs video endoscope embodiments that include a flexible tip that is controlled by manipulating a control lever in a handle of the endoscope device. Consistent with implementations described herein, the video endoscope includes a number of components for ensuring accurate and reproducible positioning of the flexible tip. In particular, a the video endoscope may include a control mechanism that includes circular control wheel having a pair of control wire channels positioned on the control wheel on opposite sides of a central aperture. The control wire channels each include enclosed portions for retaining a pair of control wires within the pair of control wire channels. As described herein, a portion of a periphery of the control wheel between an egress of the control wire channels includes an extended or lobed portion for engaging each control wire as the control wheel is rotated about the central aperture to provide a variable articular ratio, at different positions relative to the control wheel.

Consistent with a further implementation, the control mechanism may include a brake assembly for locking the control wheel in a selected orientation. In one embodiment, the brake assembly may include a generally tubular brake drum having a portion configured to be received within a central aperture of the control wheel. A lock actuation element is configured to engage a portion of the brake drum to expand the brake drum to engage the central aperture of the control wheel.

Figure 1:
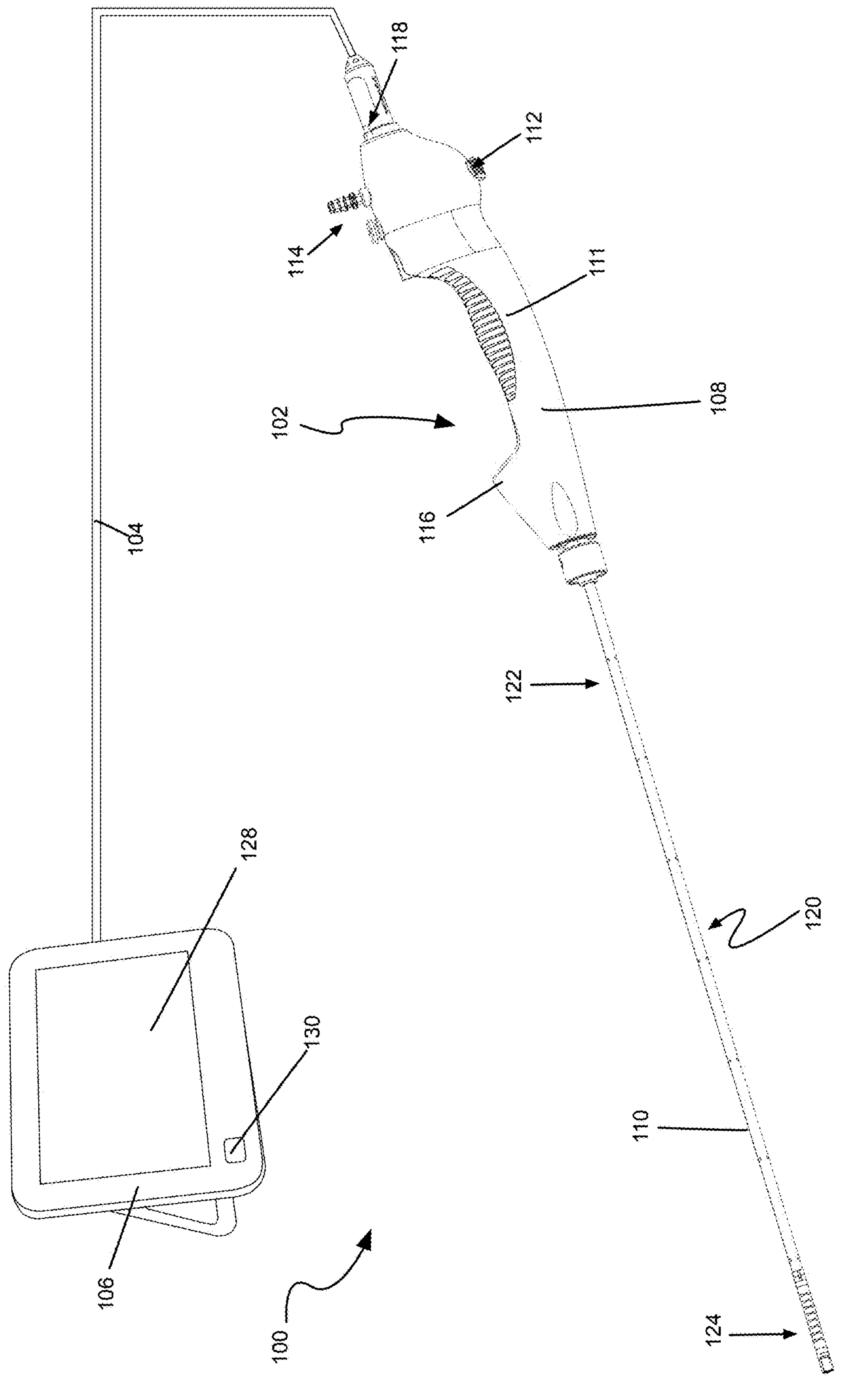
FIG. 1 is a diagram illustrating an endoscope system consistent with embodiments described herein.

FIG. 1 illustrates a video endoscope system 100 consistent with implementations described herein. As shown, video endoscope system 100 comprises an endoscope 102, a data cable 104, and a video monitor 106. As shown in FIG. 1, endoscope 102 includes a handle 108 and a shaft 110. Shaft 110 couples with and projects longitudinally from handle 108. As described in additional detail below, handle 108 may be formed of two similarly sized halves, referred to as a right shell 200 and a left shell 202, which snap or otherwise connect together along a longitudinal center line of handle 108 to form an inner cavity 203. When assembled, handle 108 includes, among other things, a grip portion 111, a control mechanism 112, a suction port assembly 114, an access port 116, and a data interface 118. Shaft 110 includes a distal end 119, an intermediate portion 120, and a proximal end 122 relative to handle portion 108. Distal end 119 includes a flexible tip 124. Consistent with implementations described herein, dimensions of shaft 110 (e.g., length, outside diameter, and inside diameter) may vary based on an intended use of endoscope 102, such as intended procedures, patient size, etc.

During use, flexible tip 124 of endoscope 102 is introduced into the body cavity being inspected (such as the patient's mouth). In some embodiments, a camera module and light source module are provided at distal end 118 of shaft 110 so as to capture and transmit images of the distal end 118 and corresponding patient anatomy to video monitor 106 via data cable 104. As described below, articulation of flexible tip 124 may be enabled by one or more pull wires 206 (FIG. 2A) coupled between flexible tip 124 and control mechanism 112, wherein manipulation of control mechanism 112 causes flexible tip 124 to flex or bend in at least one plane.

Video monitor 106 may provide power to and initiate image capture from endoscope 102 via data cable 104. For example, as shown in FIG. 1, video monitor 106 may include a display 128, and a control interface 130. Practitioners (e.g., medical personnel) may interface with video monitor 106 during use to initiate image capture, freeze a particular frame, or adjust certain settings. Although not shown in the Figures, video monitor 106 may also include a data cable interface for receiving an end of data cable 104, a battery or other power source, and a remote monitor interface for enabling the view of display 128 to be transmitted to one or more other display monitors.

Consistent with embodiments described herein, shaft 110 may be formed of a number of discrete components. In particular, proximal and intermediate portions 122/120 of shaft 110 may be formed of a braided, semi-rigid polymer material having a single lumen therethrough, sized to accommodate the internal components described below. Flexible tip 124, in contrast, may be formed of an injection molded material that includes a plurality of distinct lumens and a series of articulation slits on its outer periphery.

Figure 2A:
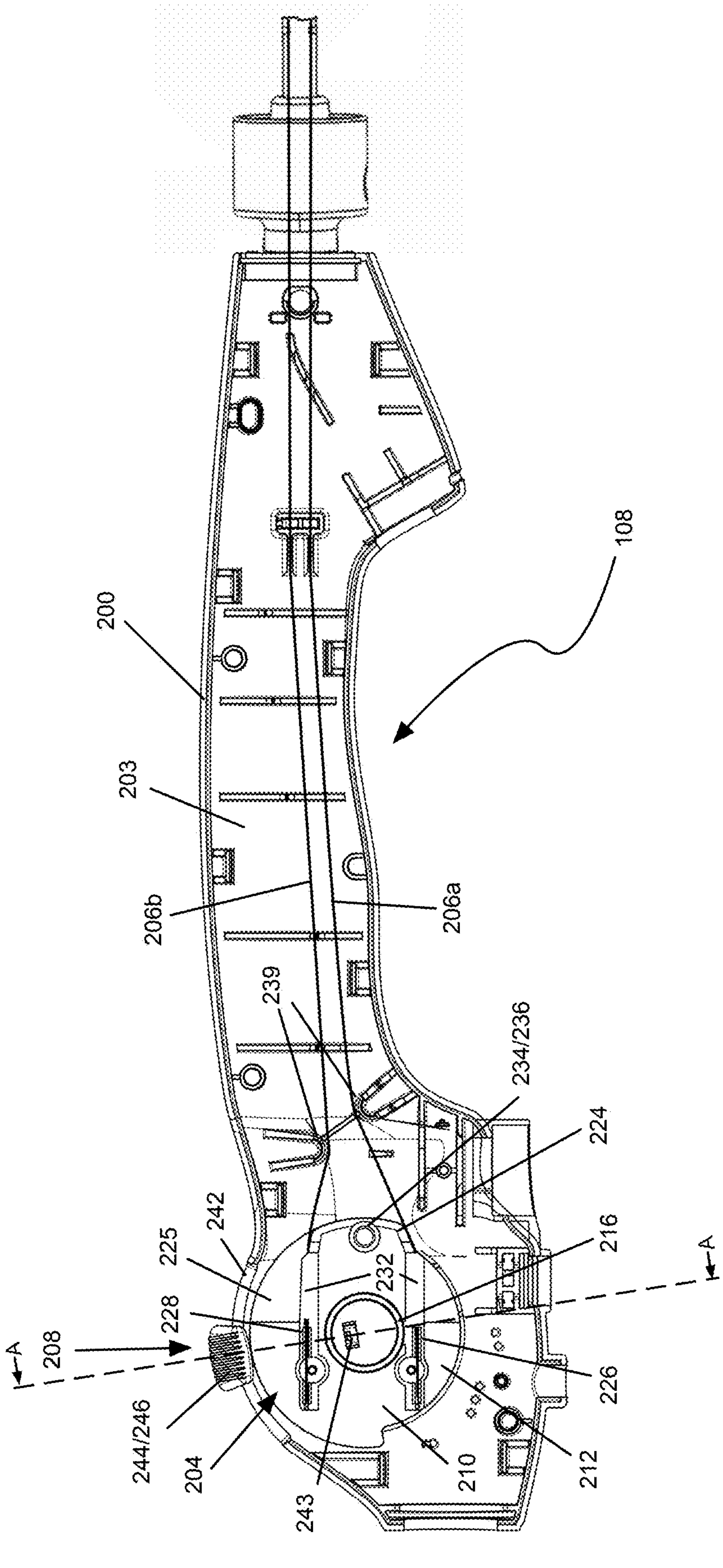
FIG. 2A is a left side view illustrating an interior of the right shell 200 and control mechanism of FIG. 1 consistent with embodiments described herein.
Figure 2B:
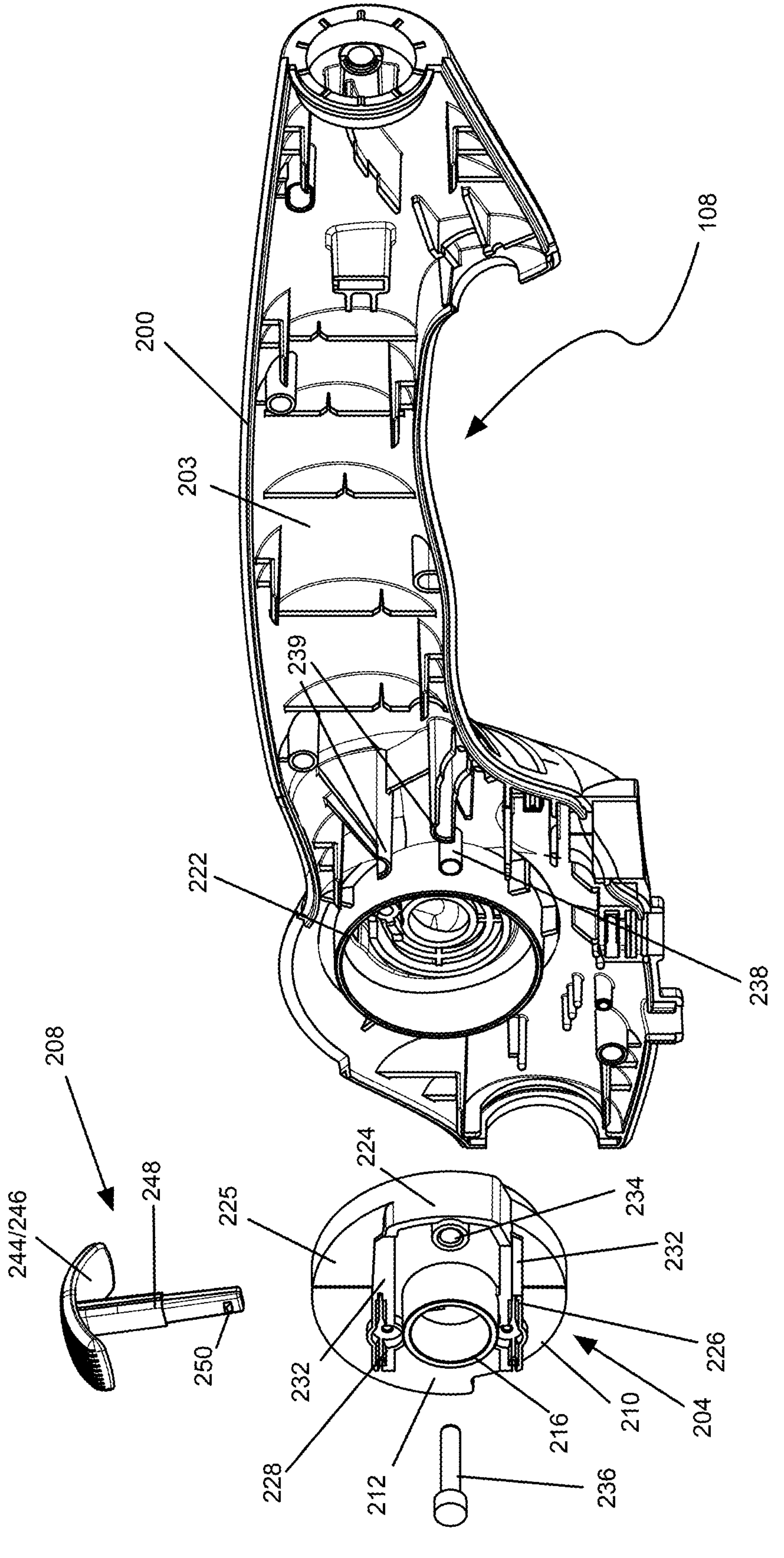
FIG. 2B is an exploded left front isometric view of the right shell and control mechanism of FIG. 2A.
Figure 2C:
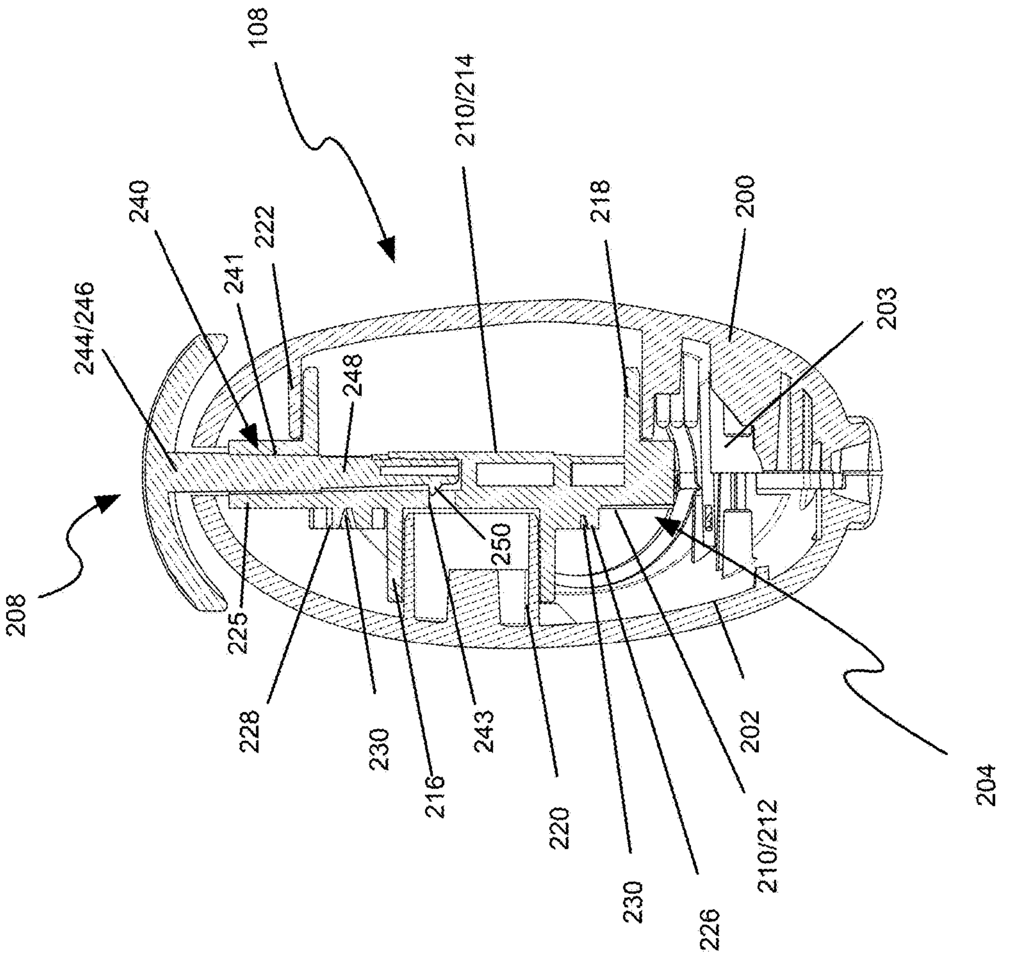
FIG. 2C is a cross sectional view of handle 108 taken along the line A-A in FIG. 2A.
Figure 2D:
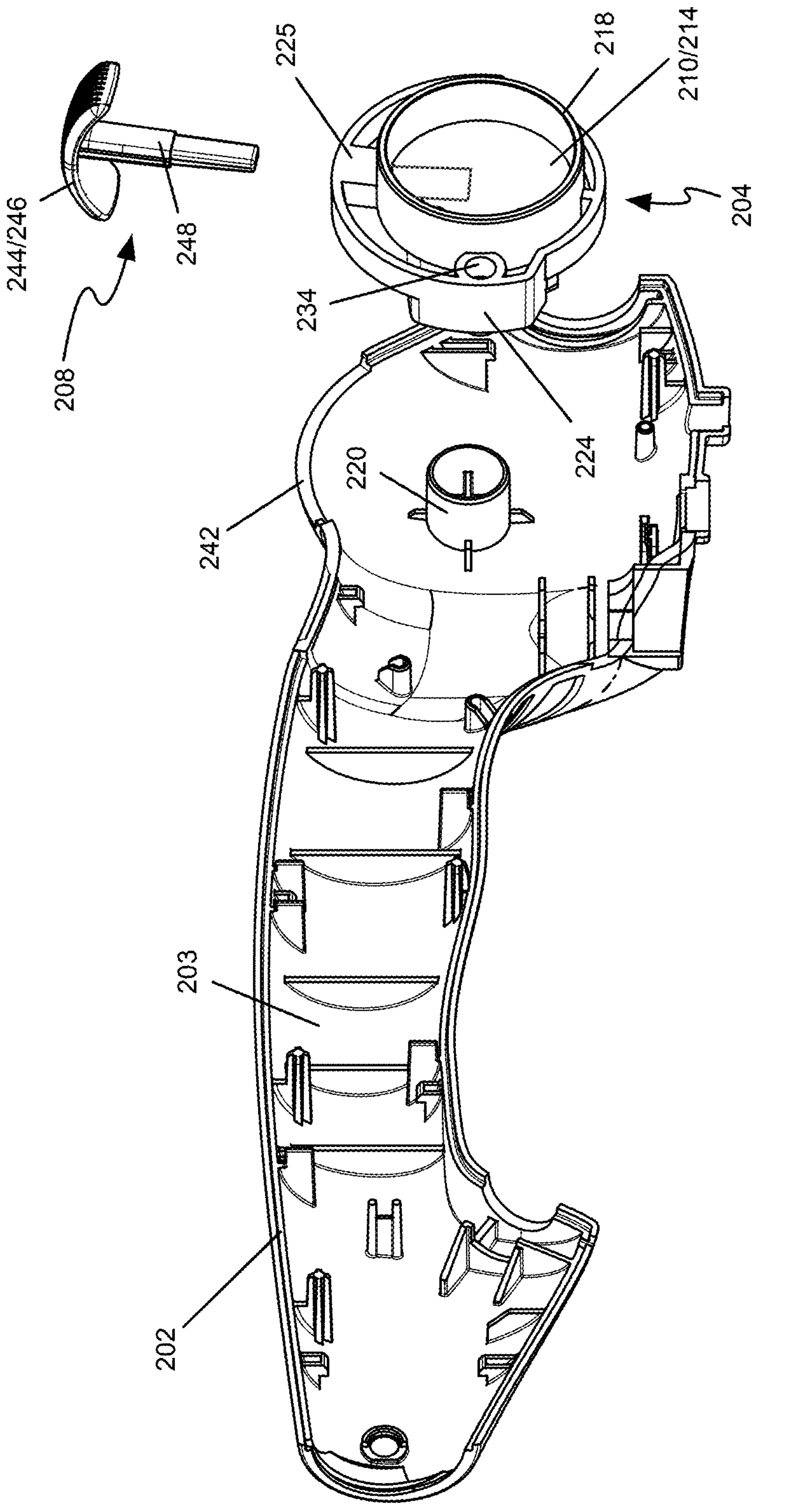
FIG. 2D is an exploded right front isometric view of the left shell and control mechanism of FIGS. 1 and 2A.

FIG. 2A is a left side view illustrating an interior of right shell 200 and control mechanism 112. FIG. 2B is an exploded left front isometric view of right shell 200 and control mechanism 112. FIG. 2C is a cross sectional view of handle 108 taken along the line A-A in FIG. 2A. FIG. 2D is an exploded isometric view of left shell 202 and control mechanism 112. As shown, in one exemplary implementation, control mechanism 112 may include a control wheel 204, a pair of pull wires 206*a* and 206*b* (referred to generally and collectively as "pull wires 206"), and a control lever 208. FIGS. 3A-3F are back, left, front, bottom, front left isometric, and back left isometric view, respectively, of control wheel 204 and control lever 208 consistent with implementations described herein.

As shown in FIGS. 2A-3F, control wheel 204 includes a generally disc-shaped body 210 rotatably mounted within inner cavity 203 of handle 108. As shown, disc-shaped body includes a left side 212 and a right side 214. In particular, in one implementation, control wheel 204 includes a left shaft portion 216 that projects leftwardly from left side 212 of disc-shaped body 210 toward left shell 202 and a right shaft portion 218 that projects rightwardly from right side 214 of disc-shaped body 210 toward right shell 200. To accommodate rotational mounting within inner cavity 203, left shell 202 may include a left-side boss 220 sized to receive left shaft portion 216 and right shell 200 may include a right-side boss 222 sized to receive right shaft portion 218. For example, an outside surface of left-side boss 220 may receive and engage an inside surface of left shaft portion 216 and an inside surface of right-side boss 222 may receive and engage an outside surface of right shaft portion 218, although alternative configurations may be made.

Figures 3A, 3B, 3C, 3D, 3E, 3F:
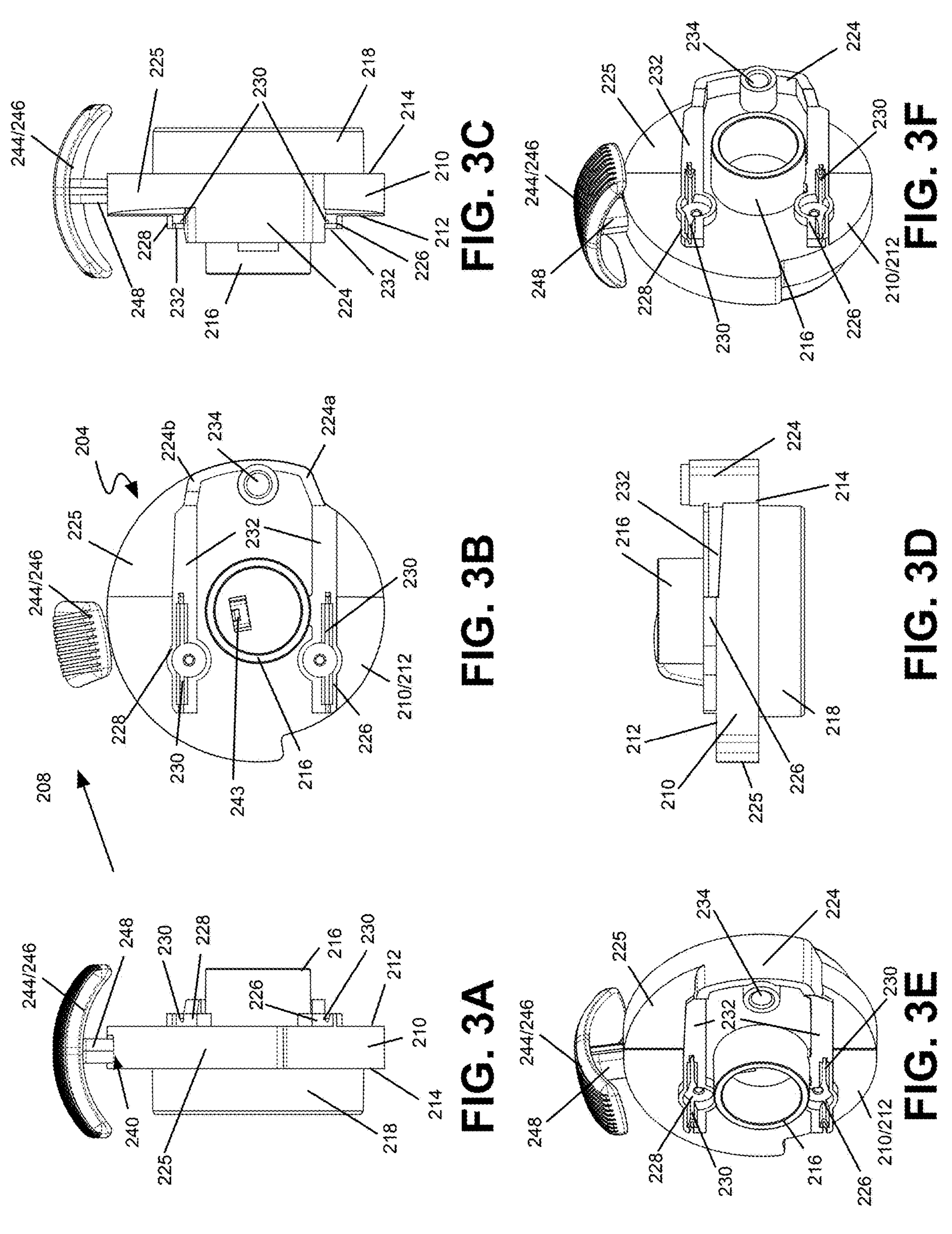
FIGS. 3A-3F are back, left, front, bottom, front left isometric, and back left isometric view, respectively, of the control wheel and control lever of FIGS. 2A-2D, consistent with implementations described herein.

Consistent with implementations described herein, disc-shaped body portion 210 includes a lobed or cam shaped configuration wherein at least a portion 224 of an outer periphery of body portion 210 projects radially outward relative to a remainder of body portion 210. Accordingly, at least a portion of control wheel 204 is provided with differing outside diameters, with a first portion having a smaller outside diameter and a second portion having a larger outside diameter. As shown in FIGS. 2A and 3A, a forward portion of body portion 210 includes lobed or extended portion 224 which effectively forms areas of increasing radius for engaging respective pull wires 206. Such a configuration allows for a variable pull ratio to be applied to pull wires 206 as control wheel 204 is rotated and as pull wires 206 engage lobed portion 224.

In addition to lobed portion 224, disc-shaped body portion 210 may further include an expanded region 225. As with lobed portion 224, expanded region 225 may also include an outside diameter larger than the remainder of body portion 210. In some implementations, an outside diameter of expanded region 225 may be the same as that of lobed portion 224, however in other embodiments, expanded region 225 may include a different (e.g., larger) outside diameter. As shown in FIG. 3E, expanded region 225 may be configured to not engage or otherwise support pull wires 206 on an outer periphery thereof, in contrast to lobed portion 224. In particular, as shown, lobed portion 224 may be formed in a region of body portion 210 that is leftward or on top of expanded region 225.

As shown in FIG. 2A, expanded region 225 may include at least portions of control wheel 204 that may become adjacent opening 242 in handle 108 through which control lever 208 extends. By including expanded region 225 in this area of handle 108, any gap between control wheel 204 and opening 242 may be minimized, thereby preventing or minimize the entry of foreign materials into inner cavity 203.

As shown in the figures, body portion 210 of control wheel 204 includes a pair of pull wire troughs 226 and 228 for receiving and securing pull wires 206*a* and 206*b*, respectively, therein. As shown in FIGS. 3E and 3F, pull wire troughs 226/288 may be formed as parallel projections extending from a left surface of body portion 210 in an orientation generally perpendicular to an axis of rotation of control wheel 204 and on opposite sides of left shaft portion 216. Pull wire troughs 226 and 228 may be formed adjacent opposing portions 224*a* and 224*b* of lobed portion 224, so that forward ends of troughs 226/228 terminate adjacent opposing portions 224*a* and 224*b* of lobe portion 224, respectively.

As shown, pull wire troughs 226 and 228 are formed on opposite sides of left shaft portion 216, such that rotation of control wheel 204 about left shaft portion 216 in a clockwise direction causes pull wire 206*a* to retract relative to endoscope shaft 110 and pull wire 206*b* to travel further into endoscope shaft 110, thus deflecting tip 124 downwardly relative to handle 108. Conversely, rotation of control wheel 204 about left shaft portion 216 in a counterclockwise direction causes pull wire 206*a* to travel further into endoscope shaft 110 and pull wire 206*b* to retract relative to endoscope shaft 110, thus deflecting tip 124 upwardly relative to handle 108.

As shown in FIGS. 2A and 3A, in one implementation, troughs 226/228 may be formed asymmetrically relative to left shaft portion 216, with trough 226 being formed closer to left shaft 216 than trough 228. However, as shown, the positioning of opposing portions 224*a* and 224*b* of lobed portion 224 establishes the deflection geometry for effecting movement of pull wires 206. In particular, in the embodiment illustrated, a distance from the center of left shaft portion 216 (i.e., the center of disc-shaped body portion 210) to each of portions 224*a* and 224*b* are identical. In this manner, rotation of control wheel 204 about left shaft portion 216 in either clockwise or counterclockwise directions results in an equal amount of movement of pull wires 206. In contrast, in other implementations, portions 224*a* and 224*b* may be asymmetrically positioned, such that movement of pull wires is biased in a particular direction.

Each pull wire trough 226/228 includes a channel 230 therein for receiving its respective pull wire 206 upon assembly of endoscope 102. Channels 230 may be sized to accommodate pull wires 206. In some implementations, channels 230 may include a v-groove configuration for seating each pull wire 206 at a particular position relative to channel 230. Consistent with implementations described herein, each pull wire trough 226/228 includes an enclosing portion 232 for covering at least a portion of the channels 230 within troughs 226/228. Such a configuration prevents pull wires secured within troughs from falling out of channel 230 and becoming disengaged from lobed portion 224 prior to or during use. In some embodiments, enclosing portion 232 may extending forwardly from troughs 226/228 up to the outer periphery of control wheel 204 to prevent pull wires 206 from becoming disengaged from control wheel 204.

In some implementations, body portion 210 of control wheel 204 may be provided with a tensioning pin aperture 234 for receiving a tensioning pin 236 therethrough during assembly of endoscope 102. As shown in FIG. 2B, tensioning pin aperture 234 may be configured to align with tensioning pin boss 238 provided in right shell 200, so that tensioning pin 236 may be received into tensioning pin boss 238 through tensioning pin aperture 234 during assembly of endoscope 102 to fix the rotation of control wheel 204 relative to right shell. When rotationally fixed, pull wires 206 may be received within channels 230 and their respective tensions may be adjusted to obtain a neutral setup, with pull wires 206*a* and 206*b* exhibiting equivalent tension. Once such a neutral setup is achieved, pull wires 206 may be secured within troughs 226/228, such as via a glue, or suitable clamping mechanism. In one implementation, a self-curing adhesive or UV-curable glue may be applied to pull wires 206 within throughs 226/228 and allowed to cure or UV cured. At this point in the assembly, tensioning pin 236 may be removed, thus allowing control wheel 204 to rotate freely relative to handle 108.

As shown in FIGS. 2A and 2B, to facilitate accurate routing of pull wires 206 through handle 108, one or both of shells 200/200 may include routing posts 239 which project inwardly and include an arcuate configuration for guiding pull wires 206 and preventing unnecessary wear or binding. As shown, routing posts 239 may be positioned at particular intermediate locations within handle 108 to provide longitudinal paths through handle 108 that avoid interference with other features included within handle 108, such as conduit or tubing associated with suction port assembly 114 or an access port 116, grip portion 111, etc., which are not shown in the figures. As shown in FIG. 2A, such locations may not symmetrically align with pull wire troughs 226/228.

As shown in FIGS. 3A and 2C, control wheel 204 further includes a control lever engagement portion 240. Control lever engagement portion 240 includes a radially inward slot 241 formed in a periphery of body portion 210 of control wheel 204 and configured to align with a corresponding opening 242 in handle 108. As shown in FIG. 2C, opening 242 in handle 108 may be created by corresponding slots in right shell 200 and left shell 202. In some implementations, control level engagement portion 240 may include a clip element 243 for allowing releasable engagement with a corresponding clip portion of control lever 108, as described below. In other implementations, control lever 108 may be secured within control level engagement portion 204 by other means, such as adhesive, a friction fit, etc.

As shown in FIG. 2B, control lever 208 may include a generally T-shaped body 244 having an engagement portion 246 and a shaft portion 248 that projects downwardly from engagement portion 246. As shown, engagement portion 246 may be configured for easy forward/backward manipulation by a user's thumb during operation of endoscope 102. In some embodiments, engagement portion 246 includes a curved lateral profile that generally mirrors an outer configuration of handle 108. Such a feature minimizes the likelihood that control lever 108 will get caught up on various environmental elements, such as clothing, equipment, wires/cables, etc. An outer surface of control lever 108, may include a friction surface, such as ribbed, grooved, or knurled surface. Such a configuration reduces the likelihood that a user's thumb will slip off of control lever 108 during use. Shaft portion 248 of control lever 208 may include an external configuration that corresponds to slot 241 in control lever engagement portion 240, which may include a rectangular, cylindrical, or tapered configuration. As briefly described above, shaft portion 248 may include a clip feature 250 to facilitate releasable coupling of control lever 208 to control wheel 204. Although a T-shaped body is shown in the figures, in other embodiments, additional or alternative configurations may be used, such as a generally cylindrical or bulbous knob, etc.

As briefly described above, control lever engagement portion 240 of control wheel 204 includes a clip element 243 configured to enable removable coupling of control lever 112 therewith. For example, as shown in FIG. 3A, clip element 243 may include an opening or aperture in body portion 210 of control wheel 204 configured to align with the radially inward slot 241 in control lever engagement portion 240 at a position aligned with clip feature 250 on control lever shaft portion 248, when control lever shaft portion 248 is full seated within. As shown in FIG. 2C, a width of slot 241 at its distal end may be slightly wider than a width of the distal end of shaft 248, such that shaft 248 may resiliently deflect to allow at least a portion of clip feature 250 to engage clip element 243.

Figure 4A:
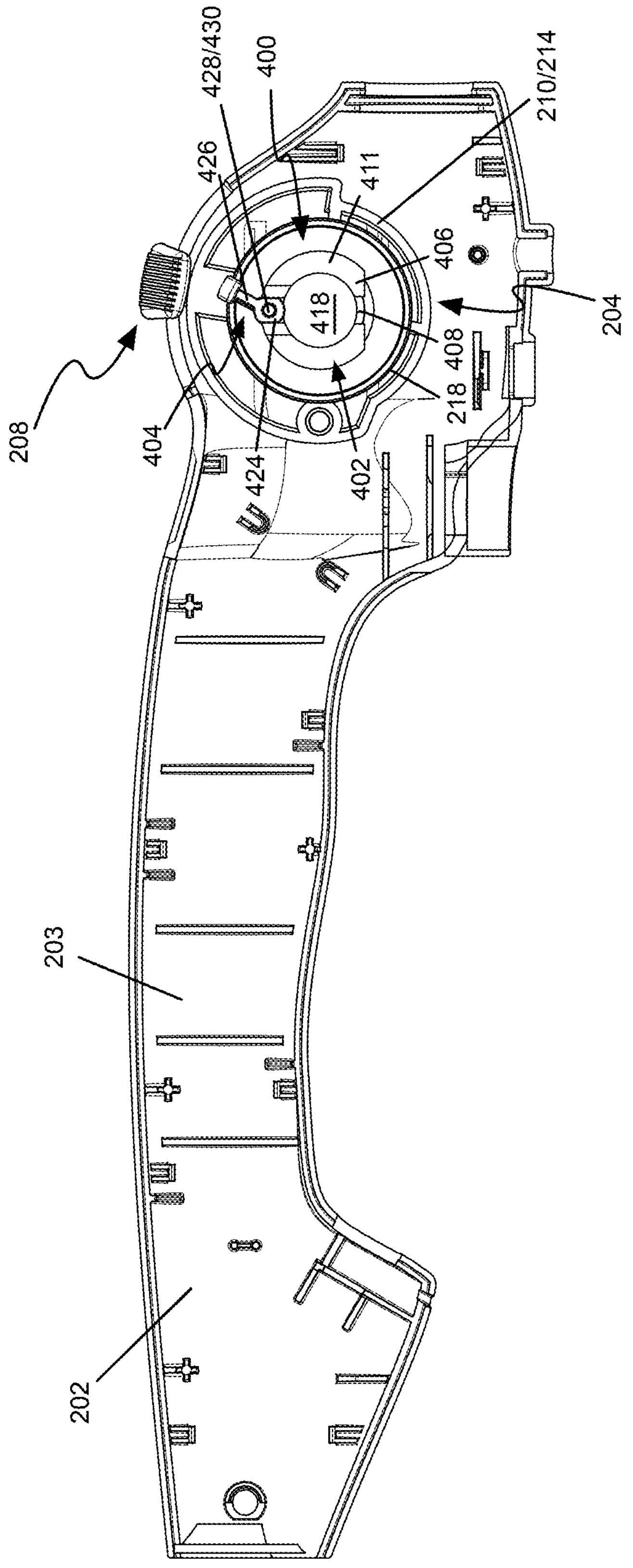
FIG. 4A is a right side view illustrating an endoscope having a lock assembly consistent with an additional embodiment described herein.
Figure 4B:
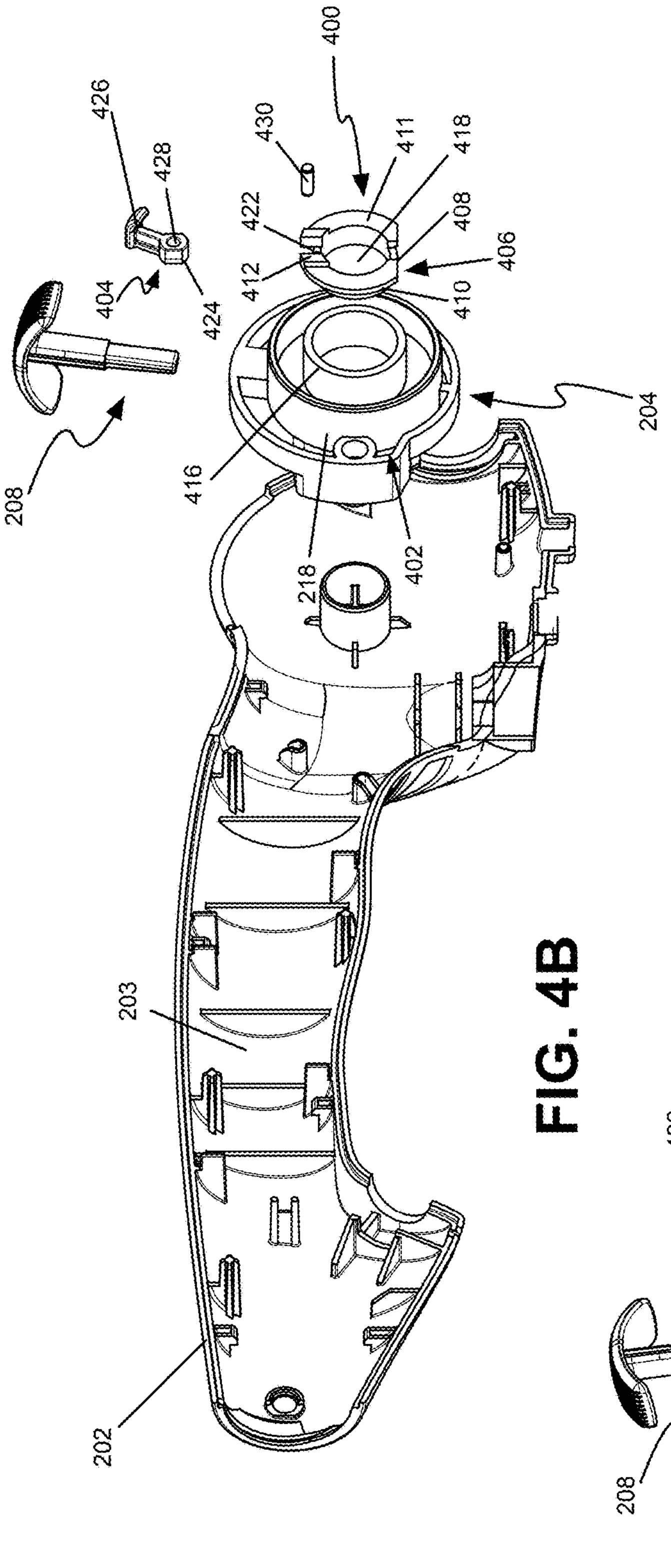
FIG. 4B is an exploded right front isometric view illustrating the lock assembly of FIG. 4A.
Figure 4C:
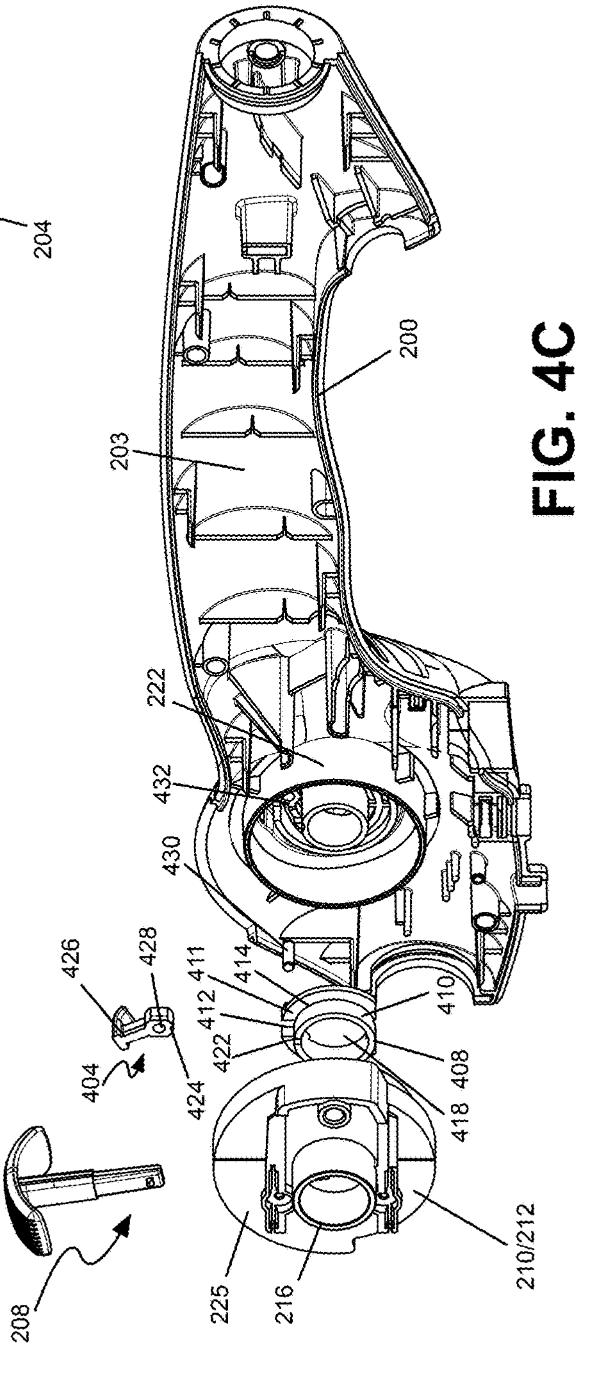
FIG. 4C is an exploded left front isometric view illustrating the lock assembly of FIGS. 4A and 4B, consistent with embodiments described herein.
Figure 4D:
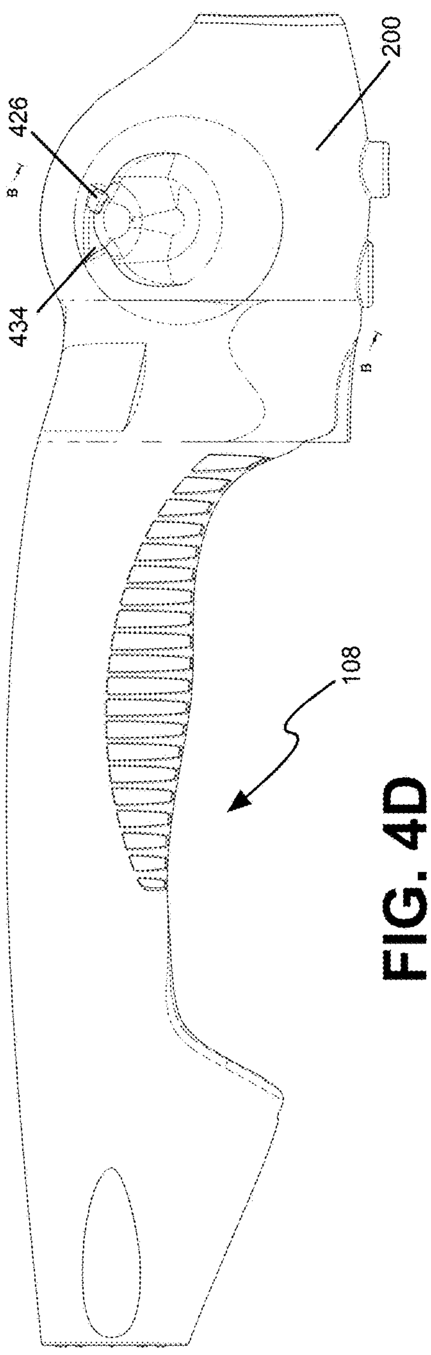
FIG. 4D is a right side view illustrating the lock assembly of FIGS. 4A-4C.
Figure 4F:
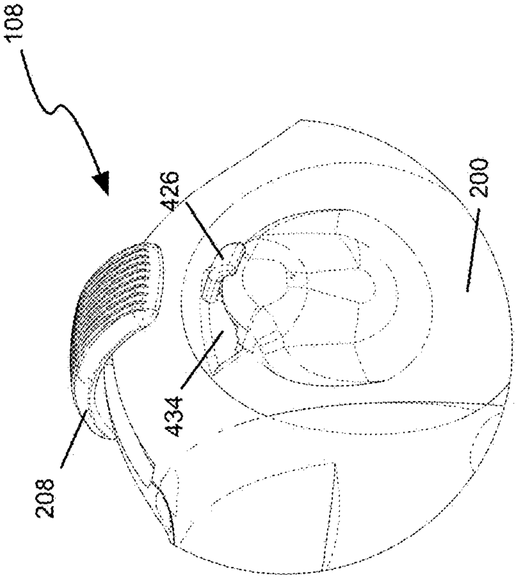
FIG. 4F is a partial left front isometric view of the handle of FIG. 4E.
Figure 4E:
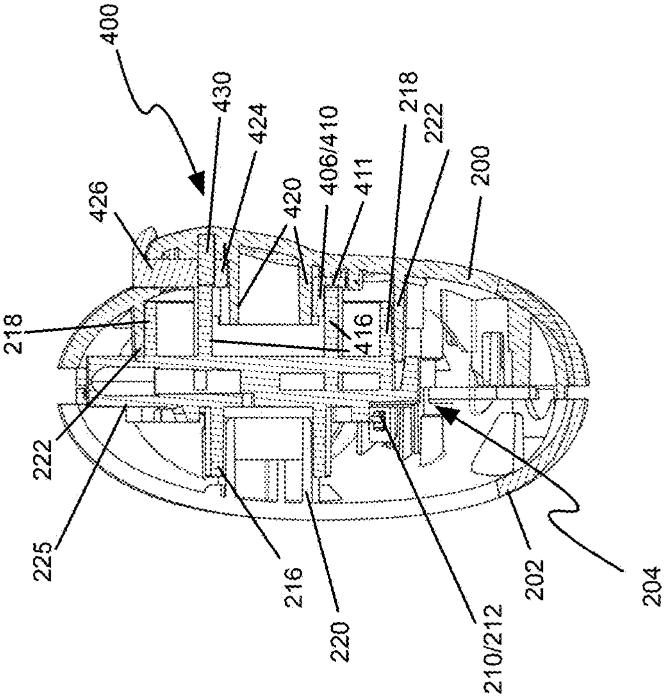
FIG. 4E is a cross sectional view of the handle of FIGS. 4A-4D taken along the line B-B in FIG. 4D.

FIG. 4A is a right side view illustrating an interior of left shell 202 and control mechanism 112 illustrating a lock assembly 400 consistent with an additional embodiment described herein. FIG. 4B is an exploded right front isometric view illustrating the lock assembly 400 of FIG. 4A. FIG. 4C is an exploded left front isometric view illustrating an interior of right shell 200 and illustrating lock assembly 400 consistent with embodiments described herein. FIG. 4D is a right side view of handle 108 illustrating lock assembly 400. FIG. 4E is a cross sectional view of handle 108 taken along the line B-B in FIG. 4D. FIG. 4F is a partial left front isometric view of handle 108 shown in FIG. 4E.

As shown in FIGS. 4A-4F, lock assembly 400 may include a brake component 402 and a lock lever 404. In the illustrated embodiment, brake component 402 comprises a generally ring-shaped body 406 formed as a single component, which includes a hinge portion 408, a friction portion 410, a flange portion 411, and a lock lever engagement portion 412.

Figures 5A, 5B, 5C:
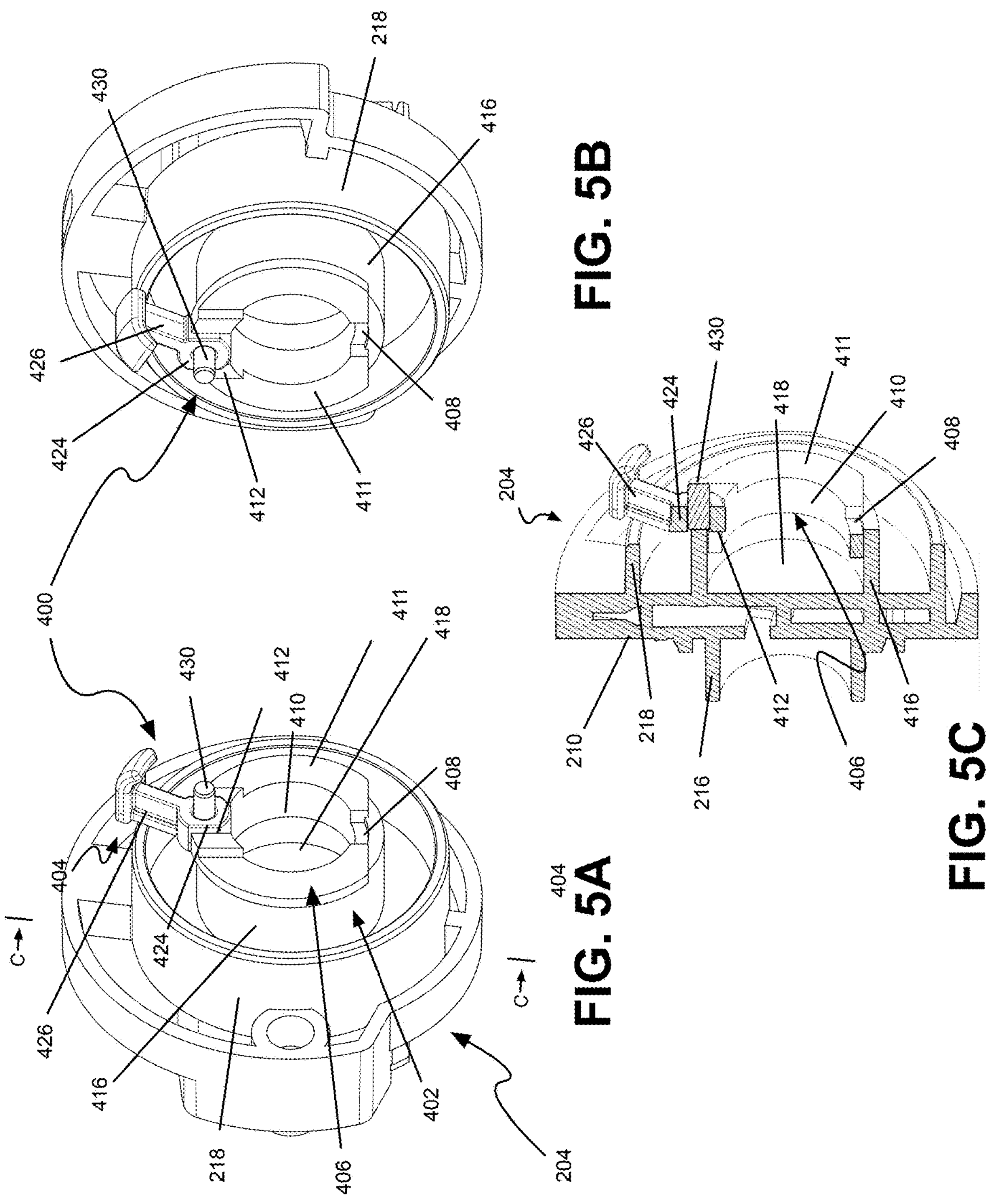
FIGS. 5A and 5B are right front isometric and right back isometric views, respectively, of the control wheel and brake component of FIGS. 4A-4E.
FIG. 5C is a cross-sectional view of the control wheel and brake component taken along the line C-C in FIG. 5A.
Figure 5D:
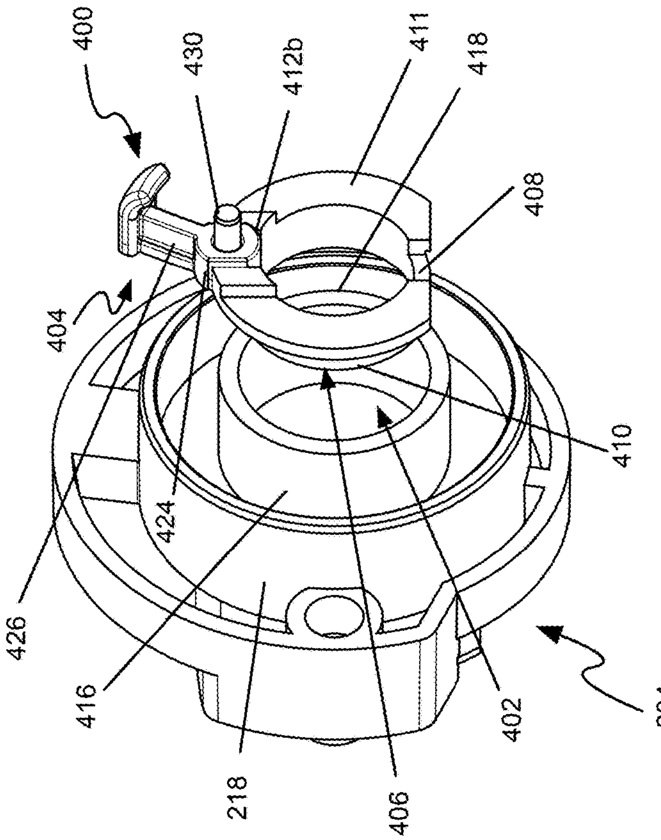
FIGS. 5D and 5E are right front and right back partially exploded isometric views, respectively, of the control wheel and brake component of FIGS. 5A-5C.
Figure 5E:
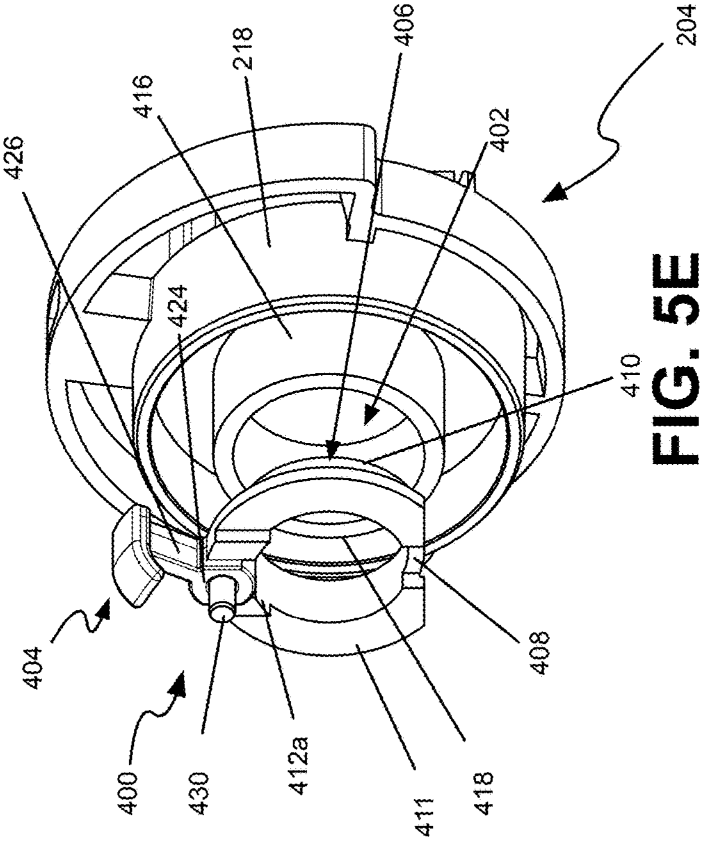
Figure 5F:
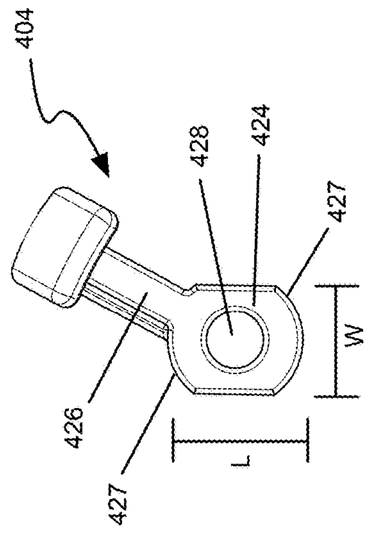
FIG. 5F is a right side view of the lock lever of FIGS. 5A-5D.
Figure 5H:
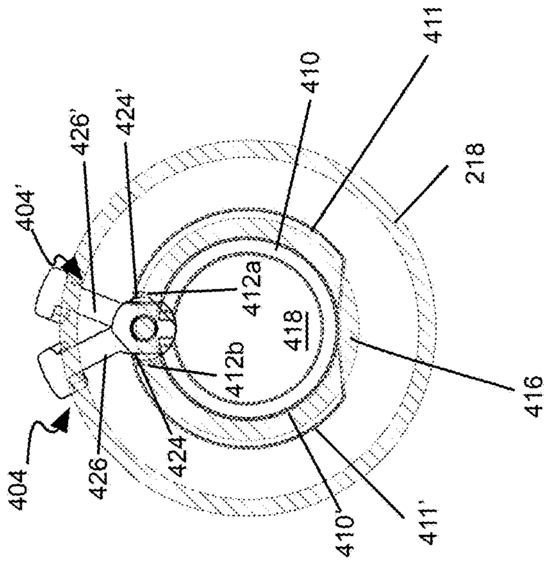
FIG. 5H is a right side partial cross-sectional view of the control wheel and lock assembly of FIGS. 4A-5D depicting both unlocked and locked configurations.
Figure 5G:
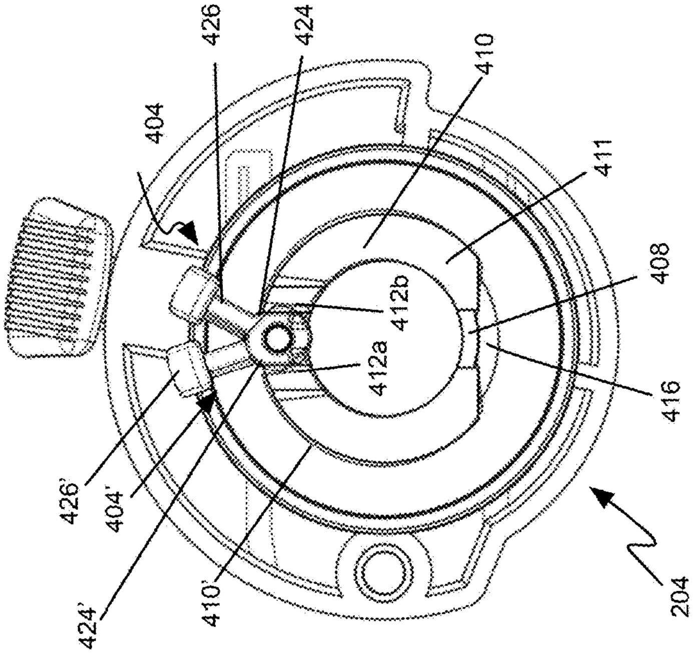
FIG. 5G is a right side view of the control wheel and lock assembly of FIGS. 4A-5D depicting both unlocked and locked configurations.

FIGS. 5A and 5B are right front isometric and right back isometric views, respectively, of control wheel 204 and brake component 402. FIG. 5C is a cross-sectional view of control wheel 204 and brake component 402 taken along the line C-C in FIG. 5A. FIGS. 5D and 5E are right front and right back partially exploded isometric views, respectively, of control wheel 204 and brake component 402. FIG. 5F is a right side view of lock lever 404. FIG. 5G is a right side view illustrating control wheel 204 and lock assembly 400 depicting both unlocked and locked configurations. FIG. 5H is a right side partial cross-sectional view of control wheel 204 and lock assembly 400 depicting both unlocked and locked configurations.

As shown in the figures, flange portion 411 projects radially outwardly from friction portion and includes a shoulder 414 for slidingly engaging an end of a brake shaft 416 that projects rightwardly from control wheel body 210 concentrically with right shaft portion 218. As shown, friction portion 410 of ring-shaped body 406 includes a central aperture 418 formed through friction portion 410 and flange portion 411 having an inside diameter generally corresponding to an outside diameter of a brake boss 420 that projects leftwardly from right shell 200 and which is concentric with right-side boss 222 and brake shaft 416. In its relaxed or default state, an outside diameter of friction portion 410 is sized slightly smaller than an inside diameter of brake shaft 416, such that in an unlocked configuration, brake shaft 416 freely rotates relative to friction portion 410. Such a configuration may be accomplished by forming brake component 402 of a suitably rigid material.

As shown, friction portion 410 of ring-shaped body 406 includes a gap 422 in its periphery formed opposite from hinge portion 408. Lock lever engagement portion 412 includes the exposed inside portions 412*a* and 412*b* of friction portion 410 adjacent gap 422. As shown in FIGS. 4A-5B, a portion of flange portion 411 adjacent hinge portion 408 is removed, so as to leave only friction portion 410 having a radially thin configuration and therefore flexible configuration. Such a configuration allows hinge portion 408 to flex when a width of gap 422 is increased, such as upon exertion of outward pressure onto lock lever engagement portions 412 via lock lever 404.

As shown, friction portion 410 is sized relative to brake shaft 416 to allow free rotation of control wheel 204 relative to ring-shaped body 406 when lock lever 404 and body 406/friction portion 410 are in an unlocked configuration. However, when friction portion 410 is placed into a locked configuration, such as via outward pressure on inside portions 412*a*/412*b* of lock lever engagement portion 412, friction portion 410 may frictionally engage an inside surface of brake shaft 416, thereby preventing rotation of control wheel 204, which in turn prevents further deflection of flexible tip 124. Consistent with implementations described herein, a texture or material of the outer surface of friction portion 410 may be configured to increase or decrease the frictional engagement with inside surface of brake shaft 416 depending on the application or type of procedure in which the device is being used. For example, a rough texture or material may be applied to the outside surface of friction portion 410 and/or inside surface of brake shaft 416 to increase friction between friction portion 410 and brake shaft 416 upon contact, whereas in other implementations, a more smooth or slick surface treatment may be applied so as to decrease the friction on contact, which consequently requires increased pressure to effect stoppage of control wheel 204. Accordingly, consistent with this description, friction surfaces of friction portion 410 and/or brake shaft 416 may be tuned (e.g., increased or decreased) to provide desired functionality and safety accordingly for any given endoscopic procedure.

As shown in FIGS. 4A, lock lever 404 comprises a lock actuation portion 424 and a lever portion 426. Lock actuation portion 424 includes a generally rectangular or oval configuration having a length “L” and a width “W”, in which the length being greater than the width to create effective cam surfaces as lock actuation portion 424 rotates within gap 422. Relative dimensions of length to width may be selected to provide desirable lock lever actuation performance. For example, a greater ratio of length to width causes friction portion 410 in brake component ring-shaped body 406 to engage brake shaft 416 with a shorter movement of lever portion 426, while a smaller ratio of length to width causes friction portion 410 in brake component ring-shaped body 406 to engage brake shaft 416 with a longer movement of lever portion 426. In all cases, the length of lock actuation portion 424 is selected so as to be sufficient to cause an amount of expansion of friction portion 410 necessary to arrest rotation of control wheel 204. In one implementation, corners 427 of lock actuation portion 424 are curved to allow for a smooth transition between unlocked and locked configurations. Lock actuation portion 424 further includes a central aperture 428 for receiving a lock lever pivot pin 430 therethrough. As shown in FIGS. 4B and 4E, right shell 200 includes a pivot pin receiving aperture 432 for receiving pivot pin 430 and which allows pin 430 to remain fixed relative to handle 108 during actuation.

As shown in FIGS. 4D-4F, right shell 200 is configured to include an opening 434 therein to accommodate a user operable portion of lever portion 426 projecting therethrough. Accordingly, lever portion 426 has a length suitable for projecting through opening 434 and for providing sufficient torque to actuate brake component 402, as described above. In some implementations, lever portion 426 may be angled with respect to actuation portion 424 to increase reachability or useability.

During assembly, brake component 402 may be positioned onto brake boss 420 and rotated such that gap 422 is proximate opening 434. Lock actuation portion 424 is inserted through opening 434 and into cap 422. Pivot pin 430 is then inserted through central aperture 428 and seated within pivot pin receiving aperture 432. Right shaft 218 of control wheel 204 may then be seated on right-side boss 222 such that friction portion 410 is received within brake shaft 416. Assembly of control mechanism 112 within endoscope 102 may then continue in the manner described above with respect to FIGS. 1-3F.

FIGS. 5G and 5H depict lock assembly 400 and control wheel 204 in both locked and unlocked states, where the locked state is illustrated in dashed lines. To actuate lock actuation portion 424, as shown in FIGS. 5G and 5H, lock lever 404 may be rotated about pivot pin 430 (e.g., via thumb pressure from a user) such that a portion of lock actuation portion 424 exerts outward pressure on inside portions 412*a*/412*b* of lock lever engagement portion 412 (depicted at elements 404' and 424' in FIGS. 5G and 5H). Continued rotation of lever portion 426 causes friction portion 410 to expand outwardly about hinge portion 408 (depicted at element 410' in FIGS. 5G and 5H) to engage the inside surface of brake shaft 416, thereby arresting movement of control wheel 204. Returning to the unlocked state is accomplished by reversing the rotation of lock lever 204, thus removing the outward pressure on friction portion 410 and allowing friction portion 410 to return to its relaxed configuration.

The foregoing description of embodiments provides illustration but is not intended to be exhaustive or to limit the embodiments to the precise form disclosed. In the preceding description, various embodiments have been described with reference to the accompanying drawings. However, various modifications and changes may be made thereto, and additional embodiments may be implemented, without departing from the broader scope of the invention as set forth in the claims that follow. The description and drawings are accordingly to be regarded as illustrative rather than restrictive.

As set forth in this description and illustrated by the drawings, reference is made to “an exemplary embodiment,” “an embodiment,” “embodiments,” etc., which may include a particular feature, structure or characteristic in connection with an embodiment(s). However, the use of the phrase or term "an embodiment," "embodiments," etc., in various places in the specification does not necessarily refer to all embodiments described, nor does it necessarily refer to the same embodiment, nor are separate or alternative embodiments necessarily mutually exclusive of other embodiment(s). The same applies to the term "implementation," "implementations," etc.

The terms "a," "an," and "the" are intended to be interpreted to include one or more items. Further, the phrase "based on" is intended to be interpreted as "based, at least in part, on," unless explicitly stated otherwise. The term "and/or" is intended to be interpreted to include any and all combinations of one or more of the associated items.

The word "exemplary" is used herein to mean "serving as an example." Any embodiment or implementation described as "exemplary" is not necessarily to be construed as preferred or advantageous over other embodiments or implementations.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements. Similarly, relative terms, such as right, left, forward, rearward, top, bottom, etc. are used to describe relative locations and positioning of various elements described herein and do not constitute absolute or permanent directions or positions relative to an external perspective.

No element, act, or instruction described in the present application should be construed as critical or essential to the embodiments described herein unless explicitly described as such.

What is claimed is:

1. An endoscope device, comprising:

a handle;

a shaft projecting from the handle;

a flexible tip coupled to a distal portion of the shaft;

first and second pull wires extending from the handle through the shaft and coupled to the flexible tip, wherein the handle includes a control wheel assembly coupled to proximal ends of the first and second pull wires, wherein the handle includes a control lever coupled to the control wheel assembly, wherein manipulation of the control lever causes rotation of the control wheel assembly, which then causes deflection of the flexible tip via the first and second pull wires, wherein the control wheel assembly comprises:

a control wheel having a disc-shaped body rotationally mounted within the handle and having an outer perimeter and a first surface, first and second pull wire troughs provided on the first surface for receiving the proximal ends of the first and second pull wires, respectively, wherein positioning of the first and second pull wires within the first and second pull wire troughs is performed independently to provide accurate tensioning of the first and second pull wires during assembly of the endoscope device; and a lock assembly for arresting rotation of the control wheel to restrain the flexible tip into a selected position, wherein the lock assembly comprises:

a brake component configured to frictionally engage a brake shaft projecting from the control wheel; and a lock lever configured to actuate the brake component, wherein at least a portion of the lock lever projects from the handle, wherein the brake component comprises:

a ring-shaped body configured to fit within the brake shaft, wherein the ring-shaped body comprises:

a friction portion;

a hinge portion; and a lock lever engagement portion positioned oppositely from the hinge portion, wherein the lock lever engagement portion comprises a gap for receiving at least a lock actuation portion of the lock lever therein, wherein actuation of the lock lever causes the lock actuation portion to engage the lock lever engagement portion to increase a width of the gap in the ring-shaped body, which causes the friction portion of the ring-shaped body to move radially outwardly about the hinge portion, and wherein the radially outward movement of the friction portion causes the friction portion to frictionally engage an inside surface of the brake shaft.

2. The endoscope device of claim 1, wherein the control wheel includes a central shaft or aperture about which the disc-shaped body rotates during use, and wherein the first and second pull wire troughs are provided on opposite sides of the central shaft or aperture.

3. The endoscope device of claim 2, wherein the first and second pull wire troughs are parallel to each other.

4. The endoscope device of claim 1, wherein each of the first and second pull wire troughs includes a channel therethrough for supporting the respective first or second pull wire.

5. The endoscope device of claim 4, wherein each of the first and second pull wire troughs further comprises an enclosing portion that covers at least a portion of the channel.

6. The endoscope device of claim 1, wherein each of the first and second pull wire troughs is configured to receive and retain a sealant or adhesive therein upon tensioning of the first and second pull wires.

7. The endoscope device of claim 1, wherein a periphery of the disc-shaped body proximate an end of each pull wire trough comprises a lobed portion for providing areas of increasing radius on the periphery of the control wheel.

8. The endoscope device of claim 7, wherein at least a portion of the periphery of the disc-shaped body comprises an expanded region to prevent external contaminants from entering the handle adjacent the control lever.

9. The endoscope device of claim 1, wherein the lock actuation portion includes a length and a width, wherein the length is greater than the width, wherein in an unlocked state, the width dimension is provided in the gap, and wherein actuation of the lock lever causes the lock actuation portion to rotate thereby increasing a dimension of the lock actuation portion within the gap which increase the width of the gap.

10. The endoscope device of claim 9, wherein the lock actuation portion comprises curved corners.

11. The endoscope device of claim 1, wherein at least one of the brake shaft or the friction portion comprises a textured surface.

12. An endoscope device, comprising:

a handle;

a shaft projecting from the handle;

a flexible tip coupled to a distal portion of the shaft; and first and second pull wires extending from the handle through the shaft and coupled to the flexible tip, wherein the handle includes a control assembly coupled to proximal ends of the first and second pull wires, wherein the handle includes a control lever coupled to the control assembly, wherein manipulation of the control lever causes rotation of the control assembly, which then causes deflection of the flexible tip via the first and second pull wires, wherein the control assembly comprises:

a control wheel having a disc-shaped body rotationally mounted within the handle; and a lock assembly for arresting rotation of the control wheel to restrain the flexible tip into a selected position, wherein the lock assembly comprises:

a brake component configured to frictionally engage a brake shaft projecting from the control wheel; and a lock lever configured to actuate the brake component, wherein at least a portion of the lock lever projects from the handle, wherein the brake component comprises:

a ring-shaped body configured to fit within the brake shaft, wherein the ring-shaped body comprises:

a friction portion;

a hinge portion; and a lock lever engagement portion positioned oppositely from the hinge portion, wherein the lock lever engagement portion comprises a gap for receiving at least a lock actuation portion of the lock lever therein, wherein actuation of the lock lever causes the lock actuation portion to engage the lock lever engagement portion to increase a width of the gap in the ring-shaped body, which causes the friction portion of the ring-shaped body to move radially outwardly about the hinge portion, wherein the radially outward movement of the friction portion causes the friction portion to frictionally engage an inside surface of the brake shaft.

13. The endoscope device of claim 12, wherein the lock actuation portion includes a length and a width, wherein the length is greater than the width, wherein in an unlocked state, the width dimension is provided in the gap, and wherein actuation of the lock lever causes the lock actuation portion to rotate thereby increasing a dimension of the lock actuation portion within the gap, which increases the width of the gap.

14. The endoscope device of claim 13, wherein the lock actuation portion comprises curved corners.

15. The endoscope device of claim 12, wherein at least one of the brake shaft or the friction portion comprises a textured surface.

* * * * *